United States Patent
Campagna et al.

(10) Patent No.: US 7,438,697 B2
(45) Date of Patent: Oct. 21, 2008

(54) ORTHOPEDIC CAST SYSTEM AND METHOD

(75) Inventors: Anthony J. Campagna, Roseville, MN (US); Matthew T. Scholz, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 12 days.

(21) Appl. No.: 11/235,382

(22) Filed: Sep. 26, 2005

(65) Prior Publication Data

US 2007/0073201 A1   Mar. 29, 2007

(51) Int. Cl.
*A61F 13/00*   (2006.01)

(52) U.S. Cl. .............................. 602/8; 602/6

(58) Field of Classification Search ............. 602/5, 602/6, 8

See application file for complete search history.

(56) References Cited

U.S. PATENT DOCUMENTS

| | | | |
|---|---|---|---|
| 3,816,229 A | 6/1974 | Bierbrauber | 161/67 |
| 3,896,251 A | 7/1975 | Landucci | 428/290 |
| 4,024,178 A | 5/1977 | Landucci | 260/472 |
| 4,054,592 A | 10/1977 | Dear et al. | 560/25 |
| 4,477,498 A | 10/1984 | Deiner et al. | 427/389 |
| 4,540,479 A | 9/1985 | Sakurai et al. | 204/427 |
| 4,595,518 A | 6/1986 | Raynolds et al. | 252/8.6 |
| 4,606,737 A | 8/1986 | Stern | 8/115 |
| 4,668,406 A | 5/1987 | Chang | 252/8 |
| 4,742,140 A | 5/1988 | Greenwood et al. | 526/245 |
| 4,989,593 A | 2/1991 | Campagna et al. | 128/89 |
| 5,016,622 A | 5/1991 | Norvell | 128/91 |
| 5,027,803 A | 7/1991 | Scholz et al. | 128/89 |
| 5,042,465 A | 8/1991 | Campagna et al. | 128/89 |
| 5,045,387 A | 9/1991 | Schmalz | 428/284 |
| 5,102,711 A | 4/1992 | Keller et al. | 428/71 |
| 5,180,359 A | 1/1993 | Dedo | 602/6 |
| 5,833,637 A | 11/1998 | Pong | 602/5 |
| 5,916,184 A | 6/1999 | McKeel | 602/6 |
| 5,948,707 A * | 9/1999 | Crawley et al. | 442/101 |
| 6,524,349 B2 | 2/2003 | Wittig | 8/137 |
| 6,664,354 B2 | 12/2003 | Savu et al. | 526/243 |
| 6,852,781 B2 | 2/2005 | Savu et al. | 524/168 |

FOREIGN PATENT DOCUMENTS

| | | |
|---|---|---|
| JP | 07-328058 | 12/1995 |
| KR | 10-2003-0061875 | 7/2003 |
| WO | WO 93/10732 | 6/1993 |
| WO | WO 94/23680 | 10/1994 |

* cited by examiner

*Primary Examiner*—Kim M Lewis

(57) ABSTRACT

An orthopedic cast system, including a hydrophilic inner layer; a hydrophobic outer layer having opposing surfaces adjacent to said hydrophilic inner layer, wherein the hydrophobic layer has an apparent surface energy less than about 60 dynes per centimeter; and a curable casting material disposed on one of the opposing surfaces is provided. Additionally, a method of immobilizing a body part is provided. An orthopedic cast kit is also provided.

97 Claims, 1 Drawing Sheet

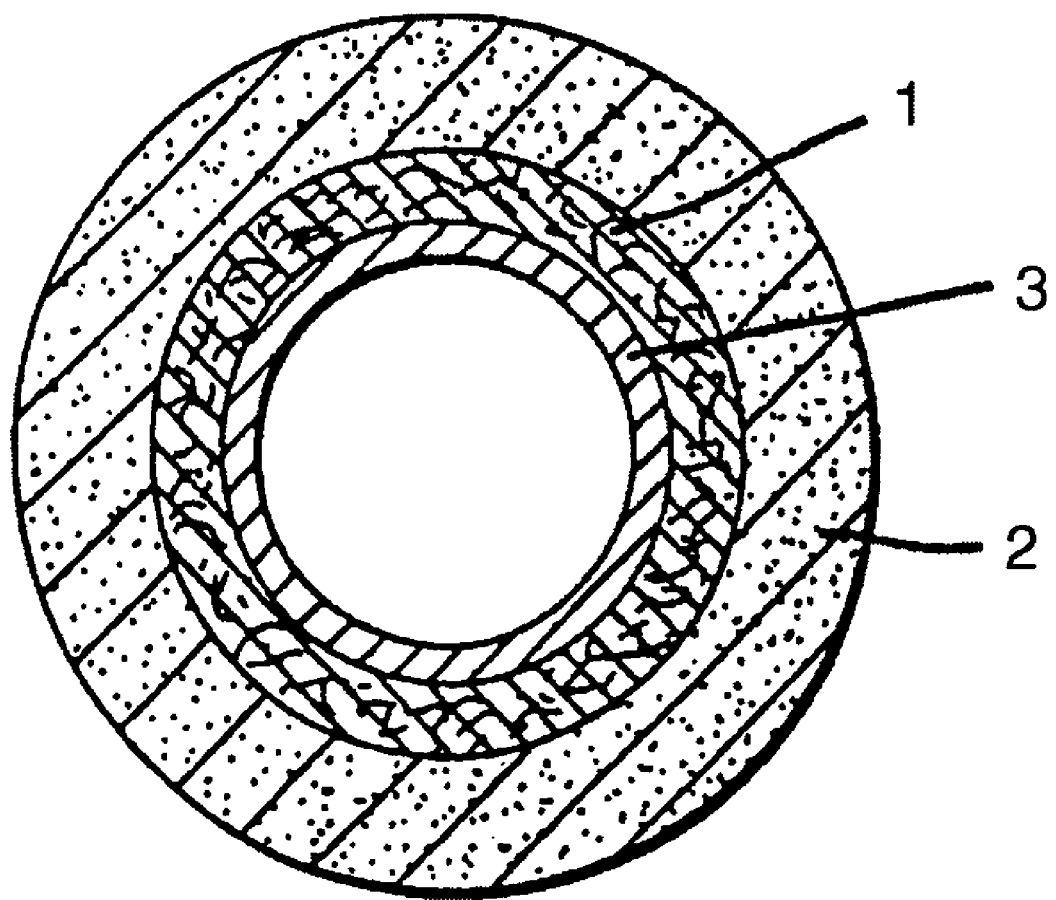

ORTHOPEDIC CAST SYSTEM AND METHOD

BACKGROUND

Casting materials used in orthopedic applications include plaster of Paris, variations thereof and curable resin systems. Casts are frequently used in combination with a soft layer of padding applied between the load-bearing casting material and the skin. Most of the plaster of Paris and curable resin systems are cured by water or aqueous catalyst systems. Generally, curing is carried out by immersing or otherwise soaking the casting material in water prior to application to the body. This process can result in wetting of the skin and any cast padding used. In use, the cast may be splashed, immersed or otherwise exposed to water, resulting in wetting of the underlying padding. Furthermore, the patient may transpire or sweat under the cast and create a humid environment under the cast that can serve as a breeding ground for microorganisms and cause serious skin breakdown. Therefore, if wetted, it is desirable that the cast padding dry as rapidly and completely as possible.

Fabrics used with casts for conventional padding materials have included cotton, foams, synthetics and wool. The major functions of the padding materials are cushioning, filing and thermal insulation. Medical uses for the padding materials include applying or relieving pressure and absorption of excess moisture. However, most padding materials lose their functionality when immersed in water.

Furthermore, conventional padding materials such as cotton and polyester are water absorbent with high apparent surface energy and tend to compress and hold water when wetted. Padding that remains wet for prolonged period scan cause skin irritation, maceration, infection and discomfort after a relatively short period of time (e.g., within 24 hours) since microorganisms such as bacteria and fungi can thrive in this environment. These conditions may also result in foul odors. Drying out wet casts with forced hot air, such as a hair dryer, is a prolonged and tedious process. Alternatively, plastic bags of various shapes can be used to prevent the cast from getting wet, but they prevent the use of any form of hydrotherapy of the injured limb.

Cast padding systems that provide microporous films, nonporous films, and composite structures adjacent to the skin are also known. Such films can feel clammy and uncomfortable for the patient. Furthermore, these systems are often not self adherent, and/or bulky, and require special techniques to wrap the limb.

It is desirable to provide a casting system with padding materials that dry rapidly if exposed to water. It is also desirable that such padding materials permit intentional wetting of the cast, for example, during bathing or discretionary exposure to water. It is also desirable that such padding materials be very comfortable for the patient to wear and/or easy for the clinician to apply.

SUMMARY OF THE INVENTION

The present invention includes an orthopedic cast system that can be wetted with water without the need for external drying sources such as hair dryers and the like. The cast system of the present invention allows the patient to bath the effected limb, if desired. The cast system of the present invention is porous and very comfortable for the patient to wear. Preferred cast systems are easy for the clinician to apply since the components once applied to the limb remain in place while the casting material is prepared and applied.

In one embodiment, an orthopedic cast system is provided including a hydrophilic inner layer; a hydrophobic outer layer having opposing surfaces adjacent to said hydrophilic inner layer, wherein the hydrophobic layer has an apparent surface energy less than about 60 dynes per centimeter; and a curable casting material disposed on one of the opposing surfaces.

In another embodiment, a method of immobilizing a body part is provided. The method includes applying a cast padding system, the cast padding system comprising; a hydrophilic inner layer; a hydrophobic outer layer having opposing surfaces adjacent to said hydrophilic layer with an apparent surface energy less than about 60 dynes per centimeter; and applying a curable casting material to one of the opposing surfaces of the cast padding system; and allowing the curable casting material to cure.

In yet another embodiment, an orthopedic cast kit is provided including a hydrophilic inner layer; a hydrophobic outer layer having opposing surfaces adjacent to said hydrophilic inner layer, wherein the hydrophobic layer has an apparent surface energy less than about 60 dynes per centimeter; and a curable casting material.

In another embodiment, an orthopedic cast kit is provided including a hydrophilic inner layer; and a hydrophobic outer layer having opposing surfaces adjacent to said hydrophilic inner layer, wherein the hydrophobic layer has an apparent surface energy less than about 60 dynes per centimeter.

BRIEF DESCRIPTION OF THE DRAWINGS

FIG. 1 depicts a cross-sectional view of an orthopedic cast system.

DETAILED DESCRIPTION OF THE INVENTION

The present invention relates to an orthopedic layered cast system that demonstrates rapid drying and water repellency is provided. The orthopedic cast system of the present invention contains a first hydrophilic layer of material, such as a stockinet, that is positioned adjacent to a body part. A second hydrophobic layer having an apparent surface energy less than about 60 dynes per centimeter is then applied. The hydrophobic layer of padding may be inherently hydrophobic or chemically treated with a substantive compound to resist wetting and/or dry more rapidly and more completely than traditional cast padding. Substantive compounds as described herein are those which remain on the cast padding under normal usage conditions to the extent necessary to provide a rapid drying cast that does not cause skin maceration. Finally, a curable casting material is then disposed on one of the opposing surfaces of the hydrophobic layer The hydrophobic layer of padding is effective even when totally immersed or water is mechanically forced into the air spaces in the padding. The rigidity of the cast system can also be improved with the use of the hydrophobic, rapidly drying cast padding, particularly when the casting materials are sensitive to water.

In one embodiment, a hydrophilic layer of padding material adjacent to a body part is provided. As used herein, the term "hydrophilic" refers to a material having affinity for water, i.e. water absorbent. If at least 3 of 5 drops of pure distilled water absorb into the material when tested according to the modification of AATC 118-1983, as described herein, then the material is considered hydrophilic. In one embodiment of the present invention, the hydrophilic layer is a composite structure, free of films. As used herein, composite structure is a laminate composed of at least two layers selected from fabrics or open cell foams.

Microporous membranes such as those described in U.S. Pat. No. 5,102,711 have very high porosity values compared to the preferred materials of the present invention. Higher porosity values indicate relatively low porosity.

In one embodiment, the hydrophilic layer of cast padding material can be manufactured from cotton, polyester, polyamides such as nylon, acrylic, rayon, polyolefins treated to be hydrophilic, and other fiber forming materials as well as fiber blends formed into nonwoven, knit, woven, or melt blown fiber constructions. Open cell foams also may be used as the hydrophilic layer as long as there is requisite porosity, basis weight, and surface energy properties as set forth herein. These materials may be inherently hydrophilic or may be treated with surfactants, emulsifiers, wetting agents, polymers or combinations thereof to render them hydrophilic. The hydrophilic layer may be treated to render it hydrophilic or may be constructed of hydrophilic components such as fibers or foam forming materials.

Mammals prefer the feeling of soft, highly porous, absorbent fabrics adjacent to the skin such as cotton, nylon, rayon, polyester, silk, wool, acrylic, as well as certain treated polyolefins, and various blends. As used herein the term fabric refers to knitted, woven, and non-woven structures formed at least in part from continuous or discontinuous fibers or filaments. Fabrics may be tubular or flat and single or multiple layers. A preferred fabric is a tubular stockinet. These fabrics preferably are highly porous with low porosity values as described in the Examples below.

The hydrophilic layer is preferable free of a film. As used herein, a film is a continuous sheet which may be solid or microporous. Microporous films are often referred to as membranes.

Fabrics preferably allow actual air flow rather than only vapor transmission. Fabrics used for the hydrophilic layer generally have a porosity defined as the passage of 100 cc of air to pass through a one square inch single layer of the padding material at 74-76° C. and 50% relative humidity in less than 60 seconds, when tested using a W & L. E. Gurley Densiometer Model 4110 (Troy, N.Y.) as described herein. Preferably, the fabrics have a porosity less than 30 seconds, more preferably in less than 15 seconds, and most preferably in less than 5 seconds. The porosity provided by the hydrophilic layer allows the injured limb to dissipate heat, transpire without moisture build up, and dry rapidly when wetted.

Basis weight is another property of the material used as the hydrophilic layer. A relatively low basis weight hydrophilic layer will generally provide a soft lightweight conformable fabric next to the skin, higher air permeability, less insulation and thus be cooler to wear and ensure rapid dry out. For certain embodiments, the hydrophilic layer has a basis weight of at least 50 grams/$M^2$, preferably at least 100 g/$M^2$, and more preferably at least 150 g/$M^2$, when measured in a stretch condition as described in the examples below. For certain embodiments, the hydrophilic layer has a basis weight of no greater than 500 grams/$M^2$, preferably no greater than 400 g/$M^2$, and more preferably no greater than 300 g/$M^2$ when measured in a stretch condition as described in the examples. A preferred fabric has a basis weight of 175 to 225 g/$M^2$ when measured in a stretch condition as described in the examples below.

The hydrophilic layer of padding material has an apparent surface energy greater than 60 dynes/cm and preferably greater than 70 dynes/cm. The hydrophilic layer of padding material of the orthopedic cast system of the present invention can be prepared from any hydrophilic material conventionally used against the skin in the apparel industry.

In one embodiment, the hydrophilic layer of padding material of the orthopedic cast system also contains a discontinuous coating of an elastomer. For discontinuous coatings, a pattern selected for the application of the elastomeric material may intentionally be directionally asymmetric in order to provide for different coefficients of friction in multiple directions (e.g., directions parallel to the plane of the material and perpendicular to each other) on the padding material as disclosed in U.S. Pat. No. 5,948,707 (incorporated herein by reference). This condition may be particularly desirable for certain applications that might benefit from increased resistance to slippage in one direction while allowing a greater amount of slippage in another direction.

The elastomeric material should be adequately soft to provide the necessary gripping capability and comfort for use in contact with the skin or another fabric surface. Typically, if a non-slip application is required and involves contact with another fabric rather than direct skin contact, an elastomer of lower elastic modulus may be necessary to allow for easy bending, curling, or conforming. The phrase "non-slip" is used generally herein to describe a waterproof, water vapor permeable fabric having a surface which has been modified as described above resulting in substantially reduced slippage when used in contact against human skin or another fabric or other surface. The selection of elastomer, the type of application pattern of the elastomer, as well as the percentage of area coverage can be readily determined by one skilled in the art for specific applications of the inventive material.

In one embodiment, the non-slip hydrophilic layer having the discontinuous coating of elastomer can be made in various forms having a static coefficient of friction of greater than about 1.0. The static coefficient of friction of this "non-slip" material may be as high as 2.5 or higher, depending on the type of elastomer, the amount of the surface provided with the elastomeric covering, and the type of pattern used. The coefficient of friction of the non-slip surface of the hydrophilic layer can be evaluated according to ASTM D 1894, Standard Test Method for Static and Kinetic Coefficients of Friction of Plastic Film and Sheeting, using a Monitor/Slip and Friction, Model 32-06 test apparatus manufactured by Testing Machines, Inc., Amityville, N.Y.

Various elastomers may be useful as the discontinuous coatings in the form of different patterns with different spacings, etc. as described above. The various elastomers include silicones, such as heat-cured silicones, condensation-cured silicones, and RTV silicones; polyurethanes; block copolymers such as KRATON elastomers; natural rubber; polyisoprene; neoprene; and the like. The elastomers may be applied by any of various methods which results in adequate bonding for the intended application.

The relatively thin hydrophilic layer is covered by a hydrophobic layer. The successive layers of cast padding systems have sufficient adhesion to each other to hold the layers in place. Preferably this adhesion is accomplished through mechanical means such as interlocking fibers rather than through the use of pressure sensitive adhesives. The hydrophobic layer may be form from a single layer or multiple layers.

The hydrophobic layer is preferably considerably thicker than the hydrophilic layer. As used herein, the term "hydrophobic" refers to a material that lacks affinity for water and tends to repel and not absorb water when tested by the Apparent Surface Energy Test. This hydrophobic layer as used herein is referred to as the "cast padding". Together the layers (which can be either hydrophobic and hydrophilic) provide effective padding to prevent the rigid casting material from harming the skin during wear or upon removal with a cast saw.

The cast padding of the present invention should be sufficiently dense to provide comfort to the patient during wear and protection during removal with a cast saw. Preferred cast padding has a basis weight of at least 40 g/M$^2$, preferably at least 60 g/M$^2$ and most preferably at least 90 g/M$^2$. The cast padding basis weight may be as high as 200 g/M$^2$ or higher. Since many of the preferred cast padding materials of the present invention are inelastic and relatively fragile the basis weight should be determined by weighing a section of completely relaxed cast padding fabric.

The cast padding is treated to possess a low surface energy. In addition to being water repellent, the cast padding also demonstrates the characteristic that water forced into the void spaces sheds rapidly when the padding possesses a low surface energy. Untreated padding stays soaked for extensive periods of time, resulting in slow and difficult drying even with a heated airstream. The treated padding dries more quickly, shedding the water in the void spaces and retaining much less water in association with the elements of the padding such as fibers. In addition to having a low surface energy, the cast padding is permeable to air and water vapor.

The cast padding should be constructed such that at least 50% the area is hydrophobic, most preferably 75% of the area is hydrophobic, most preferable 90% of the area is hydrophobic. Most preferably the entire cast padding is hydrophobic.

In one embodiment, the orthopedic cast system contains a hydrophobic layer of cast padding having opposing surfaces. The hydrophobic properties may be imparted to cast padding of the cast system by a chemical treatment which provides the elements of the padding, such as fibers, with a reduced surface energy. It has been found that low surface energy can be provided to the padding from the application of substantive compounds, such as silicones, fluorochemicals, hydrocarbons and combinations thereof. The substantive compounds are non-irritating to the skin and can be applied by solutions, sprays, or plasma vapor to the cast padding material.

Alternatively, inherently hydrophobic fibers may be used to form the hydrophobic cast padding. As used herein an inherently hydrophobic fiber is one that when free of any finish has a surface energy of less than 50 dynes/cm, preferably less than 45 dynes/cm and most preferably less than 40 dynes/cm. Inherently hydrophobic fibers form fabrics having an apparent surface energy of less than 50 dynes/cm, preferably less than 45 dynes/cm, more preferably less than 40 dynes/cm, and most preferably less than 35 dyne/cm. Fiber is synonymous with filament. It is a natural or synthetic thread-like elongated structure which may be spun into a yarn.

The hydrophobic cast padding layer also may be an open cell foam such as an polyurethane or polyurea foam. Other foam compositions may be suitable. Such foams may be inherently hydrophobic or treated with the substantive compounds described herein. They should possess an apparent surface energy of less than 50 dynes/cm, preferably less than 45 dynes/cm, more preferably less than 40 dynes/cm, and most preferably less than 35 dyne/cm. The substantive compounds may be applied after the foam is formed or prior to the foam formation process as long as the requisite apparent surface energy is attained. Preferred foam are highly porous and have a Gurley porosity value of less than 15 seconds, preferably less than 10 seconds and most preferably less than 5 seconds. Typical foams may be 1.5 to 10 mm thick when measured as described for the non-woven padding herein. Preferred foams are 3 to 6 mm thick.

Inherently hydrophobic fibers or filaments suitable for use in the cast padding include but are not limited to polyolefins (polyethyelene, polypropylene, polybutylene, poly(4-methylpentene), and the like as well as mixtures and random or block copolymers thereof) and halogenated polyolefins such as fluorinated polymers including but not limited to polytetrafluoroethylene (PTFE). One such inherently hydrophobic fiber is described in U.S. Pat. No. 6,524,349. These fabrics may be coated with various finishes if desired to enhance their feel, processability, hydrophobicity, etc.

Whether constructed of inherently hydrophobic fibers or fibers that have been treated to produce a hydrophobic surface, the cast padding has an apparent surface energy of less than 60 dynes/cm, preferably less than 50 dynes/cm, and more preferably less than 40 dyne/cm, and most preferably less than about 30 dyne/cm.

When used, the substantive compound may be present on the fibers used to form the fabric or it may be coated onto the fabric padding material to impart low surface energy. Such compounds are generally applied at low levels. Suitable amounts are between 0.001 to 0.10 parts by weight of active ingredient per part of fabric or padding. A preferred range is 0.25 to 2.5 percent by weight, i.e. 0.0025 to 0.025 grams of active ingredient per gram of fabric or padding. A more preferred range is 0.40-2.5 percent by weight. Note that water repellent finishes can be applied to the fibers after formation or added to the polymer melt during fiber formation.

These fabrics or other fabrics, yams, fibers, or filaments can be treated with low surface energy coatings including, but not limited to, hydrocarbons, silicones, fluorochemicals and combinations thereof. Hydrocarbon repellent treatments are those that comprise at least one hydrocarbon chain of at least 8 carbon atoms. Preferred hydrocarbon water-repellent finishes include an aqueous dispersion of: a hydrocarbon wax including but not limited to parafins and polyolefins; hydrocarbon waxes and a behenic acid ester of melamine; a hydrocarbon wax, C8-C-18 alkyl methacrylate/diethylaminoethyl methacrylate copolymer such as stearylmethacrylate/diethylaminoethylmethacrylate copolymer; and "OCTOWAX" 321 (an aqueous paraffin wax emulsion, from Tiarco Chemical Co., Dalton, Ga.). Other useful hydrocarbon coatings are made by Nikwax North America Inc., Seattle Wash. Surfactants based on fatty acid or fatty alcohols including fatty acid metal salts and the like also may be useful.

Mixed fluorochemical and hydrocarbon repellent finishes may also be used including a blend of wax, a diethylaminoethyl methacrylate/hexadecyl methacrylate/octadecyl methacrylate copolymer of the type disclosed in U.S. Pat. No. 4,595,518 and a fluoroalkyl acrylate/hexadecyl methacrylate/octadecyl methacrylate/vinylidene chloride copolymer disclosed in U.S. Pat. No. 4,742,140; a blend of wax, a diethylaminoethyl methacrylate/hexadecyl methacrylate/octadecyl methacrylate copolymer and a fluoroalkyl methacrylate/dodecyl methacrylate copolymer of the type disclosed in U.S. Pat. No. 4,595,518 as well as materials of the type disclosed in U.S. Pat. Nos. 6,664,354 and 6,852,781.

The amount of repellent finish, together with the necessary diluent such as water or alcohol that is applied to the fabric, is measured as wet pick-up prior to drying and curing. The wet pick-up applied to the fabric will generally be in the range of 20 to 300% by weight, and preferably 50 to 200% by weight, based on the untreated padding fabric. The "wet pick-up" refers to the weight percent of the untreated fabric that has been added. It is calculated using the following formula:

Wet (treated) weight—Dry untreated weight)/Dry untreated weight.

For example, a section of fabric weighing 10 grams dry and 20 g when wetted with the treatment composition would have a 100% wet pick up.

Typically, commercially available repellent finishes contain about 0.5 to about 40% by weight total active ingredient. In the case of silicones, the total active ingredient may be greater than 40% by weight. In this invention, the amount of active ingredient of repellent finish applied will generally be in the range of about 0.01 to 10% by weight, and preferably 0.05 to 3% by weight, of the active ingredient in the repellent finish based on the substrate (fabric).

Suitable fluorochemicals which can be used to obtain the low surface energy layers of the hydrophobic layer of the instant invention include any of the fluorochemicals known to those skilled in the art to provide water-repellency, and optionally oil repellency to natural or synthetic fibers and films.

Classes of fluorochemical agents or compositions useful in this invention include compounds and polymers containing one or more fluoroaliphatic radicals, $R_f$. In general, fluorochemical agents or compositions useful in this invention comprise fluorochemical compounds or polymers containing fluoroaliphatic radicals or groups, $R_f$. The fluoroaliphatic radical, $R_f$, is a fluorinated, stable, inert, non-polar, preferably saturated, monovalent moiety which is both hydrophobic and oleophobic. It can be straight chain, branched chain, or, if sufficiently large, cyclic, or combinations thereof, such as alkylcycloaliphatic radicals. The skeletal chain in the fluoroaliphatic radical can include catenary divalent oxygen atoms and/or trivalent nitrogen atoms bonded only to carbon atoms. Generally $R_f$ will have 3 to 20 carbon atoms, preferably 6 to about 12 carbon atoms, and will contain about 40 to 78 weight percent, preferably 50 to 78 weight percent, carbon-bound fluorine. The terminal portion of the $R_f$ group has at least one trifluoromethyl group, and preferably has a terminal group of at least three fully fluorinated carbon atoms, e.g., $CF_3CF_2CF_2$—. The preferred $R_f$ groups are fully or substantially fluorinated, as in the case where $R_f$ is perfluroalkyl, $C_nF_{2n+1}$—.

Examples of such compounds include, for example, fluorochemical urethanes, ureas, esters, amines (and salts thereof), amides, acids (and salts thereof), carbodiimides, guanidines, allophanates, biurets, and compounds containing two or more of these groups, as well as blends of these compounds.

Useful fluorochemical polymers containing $R_f$ radicals include copolymers of fluorochemical acrylate and/or methacrylate monomers with co-polymerizable monomers, including fluorine-containing and fluorine-free monomers, such as methyl methacrylate, butyl acrylate, octadecyl methacrylate, acrylate and methacrylate esters of poly(oxyalkylene) polyol oligomers and polymers, e.g., poly(oxyethylene) glycol dimethacrylate, glycidyl methacrylate, ethylene, vinyl acetate, vinyl chloride, vinylidene chloride, vinylidene fluoride, acrylonitrile, vinyl chloroacetate, isoprene, chloroprene, styrene, butadiene, vinylpyridine, vinyl alkyl esters, vinyl alkyl ketones, acrylic and methacrylic acid, 2-hydroxyethyl acrylate, N-methylolacrylamide, 2-(N,N,N-trimethylammonium)ethyl methacrylate and the like.

The relative amounts of various comonomers which can be used with the fluorochemical monomer will generally be selected empirically, and will depend on the substrate to be treated, the properties desire from the fluorochemical treatment, i.e., the degree of oil and/or water repellency desired, and the mode of application to the substrate.

Useful fluorochemical agents or compositions include blends of the various classes of fluorochemical compounds and/or polymers described above. Also, blends of these fluorochemical compounds or polymers with fluorine-free compounds, e.g., N-acyl aziridines, or fluorine-free polymers, e.g., polyacrylates such as poly(methyl methacrylate) and poly(methyl methacrylate-co-decyl acrylate), polysiloxanes and the like.

The fluorochemical agents or compositions can include non-interfering adjuvants such as wetting agents, emulsifiers, solvents (aqueous and organic), dyes, biocides, fillers, catalysts, curing agents and the like. The final fluorochemical agent or composition should contain, on a solids basis, at least about 5 weight percent, preferably at least about 10 weight percent carbon-bound fluorine in the form of said Rf groups in order to impart the benefits described in this invention. Such fluorochemicals are generally known and commercially available as perfluoroaliphatic group bearing water/oil repellant agents which contain at least 5 percent by weight of fluorine, preferably 7 to 12 percent of fluorine in the available formulations.

By the reaction of the perfluoroaliphatic thioglycols with diisocyanates, there results perfluoroaliphatic group-bearing polyurethanes. These products are normally applied in aqueous dispersion for fiber treatment. Such reaction products are described in U.S. Pat. No. 4,054,592, incorporated herein by reference.

Another group of suitable compounds are perfluoroaliphatic group-bearing N-methylol condensation products. These compounds are described in U.S. Pat. No. 4,477,498, incorporated herein by reference where the emulsification of such products is dealt with in detail.

The perfluoroaliphatic group-bearing polycarbodimides are, e.g., obtained by reaction of perfluoroaliphatic sulfonamide alkanols with polyisocyanates in the presence of suitable catalysts. This class of compounds can be used by itself, but often is used with other $R_f$-group bearing compounds, especially with (co)polymers. Thus, another group of compounds which can be used in dispersions is mentioned. Among these compounds all known polymers bearing fluoroaliphatic residues can be used, also condensation polymers, such as polyesters and polyamides which contain the corresponding perfluoroaliphatic groups, are considered but especially (co)polymers on the basis of e.g. $R_f$-acrylates and $R_f$-methacrylates, which can contain different fluorine-free vinyl compounds as comonomers. In DE-A 2 310 801, these compounds are discussed in detail. The manufacture of $R_f$-group bearing polycarbodiimides as well as the combination of these compounds with each other is also described in detail.

Besides the aforementioned perfluoroaliphatic group-bearing agents, further fluorochemical components may be used, for example, $R_f$-group-bearing guanidines, U.S. Pat. No. 4,540,479, $R_f$-group-bearing allophanates, U.S. Pat. No. 4,606,737 and $R_f$-group-bearing biurets, U.S. Pat. No. 4,668,406, the disclosures which are incorporated herein by reference. These classes are mostly used in combination. Others include fluoroalkyl-substituted siloxanes, e.g., $CF_3(CF_2)_6CH_2O(CH_2)_3Si(OC_2H_5)_3$.

The useful compounds show, in general, one or more perfluoroaliphatic residues with preferably at least 4 carbon atoms, especially 4 to 14 atoms each. An exemplary fluorochemical is a formulation of 70% solvents and 30% emulsified solid fluorochemical polymers. The formulation includes as solvents 11% methyl isobutyl ketone, 6% ethylene glycol and 53% water. The fluorochemical polymers are a 50/50 blend of 5/95 copolymer of butyl acrylate and $C_8F_{17}SO_2(CH_3)C_2H_4O$—$CCH=CH_2$ prepared as described in U.S. Pat. No. 3,816,229, incorporated herein by reference (see especially column 3, lines 66-68 and column 4, lines 1-11) for a 10/90 copolymer. The second component of the 50/50 blend is a copolymer prepared from 1 mole of a tri-functional phenyl isocyanate (available from Upjohn Company under the name PAPI), 2 moles of $C_8F_{17}N(CH_2CH_3)CH_2CH_2OH$ and 1 mole of stearyl alcohol prepared as described in U.S. Pat. No. 4,401,780, incorporated herein by reference (see especially Table I, $C_2$ under footnote A). Emulsifiers used are conventional commercially available materials such as polyethoxylated quaternary ammonium compounds (available under the name 5% Ethoquad 18/25 from Akzo Chemie America) and 7.5% of a 50/50 mixture of $C_8F_{17}SO_2NHC_3H_6N(CH_3)_3Cl$ and a polyethoxylated sorbitan monooleate (available from ICI Limited under the name TWEEN 80). Such fluorochemicals are non-yellowing and particularly non-irritating to the skin as well as providing articles that are stable having excellent long term aging properties.

Exemplary fluorochemicals are available under the trade designations SCOTCHGARD, SCOTCH-RELEASE, and 3M BRAND TEXTILE CHEMICAL and are commercially from the 3M Company. Other commercially available materials include materials that use fluorotelomer chemistry materials provided by DuPont (available from duPont deNemours and Company, Wilmington, Del.).

Suitable silicones for use to obtain the low surface energy layers of the instant invention include any of the silicones known to those skilled in the art to provide water repellency and optionally oil repellency to fibers and films. Silicone fluids typically consist of linear polymers of rather low molecular weight, namely about 40002-25,000. Most commonly the polymers are polydimethylsiloxanes.

For use as fluids with enhanced thermal stability, silicones containing both methyl and phenyl groups are often used. Generally, the phenyl groups make up 10-45% of the total number of substituent groups present. Such silicones are generally obtained by hydrolysis of mixtures of methyl- and phenylchlorosilanes. Fluids for use in textile treatment may incorporate reactive groups so that they may be cross-linked to give a permanent finish. Commonly, these fluids contain Si—H bonds (introduced by including methyldichlorosilane in the polymerization system) and cross-linking occurs on heating with alkali.

Examples of suitable silicones are those available from Dow-Corning Corporation such as C2-0563 and from General Electric Corporation such as GE-SS4098. Especially preferred silicone finishes are disclosed in U.S. Pat. No. 5,045,387.

It may also be possible to derivatize certain materials by covalently attaching various hydrophobic groups though direct chemical reaction, grafting and the like to render them hydrophobic. For example, cotton could be reacted with $C_8$-$C_{22}$ carboxylic acids or $C_8$-$C_{22}$ carboxylic acids halides to form the alkyl ester.

Another advantage of the orthopedic cast system of this invention is the high porosity which allows the injured limb to breathe. The porosity of the hydrophobic layer of cast padding is tested using a W & L. E. Gurley Densometer Model 4110 (Troy, N.Y.). Preferably, the hydrophobic layer of cast padding has a porosity of less than about 15 seconds when measured using a Gurley densometer. More preferably, the hydrophobic layer has a porosity less than about 11 seconds.

As shown in the Figures, FIG. 1 illustrates a hydrophobic layer of cast padding 1 is surrounded by or enclosed within, or provided as a protective layer between the skin and curable casting material 2. The curable casting material can be any material that is conventionally used as the load-bearing or immobilizing structure in an orthopedic cast. For example, the casting material may consist of a knit, woven or non-woven web or an open-cell foam that is impregnated with a curable composition. The curable composition can be any of the known curable compositions that are used in orthopedic cast applications. Suitable curable compositions include plaster of paris and water-curable, isocyanate functional prepolymers, acrylates, water curable silicone ethers, methacrylates or cyanoacrylate esters, and epoxy resins and vinyl resins. The curable resins include water-cured or heat or light-cured resins. One such suitable casting material is available under trade designation SCOTCHCAST PLUS brand casting tape, available from 3M Company, St. Paul, Minn.

The hydrophobic layer of cast padding 1 is placed or enclosed between curable casting material 2 and a hydrophilic inner layer of porous fabric or foam woven or non-woven covering 3 such as a stockinet. The stockinet is usually applied to a limb, then covered with cast padding.

In application, the hydrophilic inner layer 3 is applied to the effected limb and covering at least a portion of and preferably substantially all the area over to be immobilized. Subsequently or simultaneously therewith, a hydrophobic layer of cast padding 2 (with an apparent surface energy less than 60 dynes/cm) is applied over the hydrophilic inner layer 3. Additional layers of material may optionally be added either before or after the hydrophobic layer. Finally, a curable casting material 2 or splint is applied to the exterior surface. Preferred casting materials are conventional water curable polyurethane prepolymer tapes such as available under trade designation as SCOTCHCAST Casting Tape, also plaster of Paris, thermoplastic materials such as polycaprolactone based materials and the like. Curable cast material refers to any type of material that undergoes a change of state from a generally flowable or moldable uncured first state to a generally nonflowable or nonmoldable cured second state.

The present invention further contemplates linear and tubular products which are layered composites of hydrophilic inner layer laminated to a hydrophobic layer of cast padding. The lamination may be simply multiple layers supplied together or the layers may be thermally or adhesively bonded. Thermal bonding may be accomplished by thermal embossing, flame bonding, and the like. The hydrophilic inner layer of the present orthopedic cast system may optionally have deposited on one or both major surfaces a discontinuous coating of non-slip elastomer as described in U.S. Pat. No. 5,948,707 provided that the fabric maintains its porosity and hydrophobic properties in the uncoated regions.

The orthopedic cast system of the present invention is more comfortable, and amenable to various regimens involving hydrotherapy during the patient's healing period. This allows flexibility in treatment and helps avoid the potential negative side effects associated with the prolonged wetting of the skin.

The following examples are provided to illustrate the invention and should not be construed as limiting it in any way. The scope of the invention is defined by the claims and not by the examples or the description herein.

EXAMPLES

Test Procedures

Measuring Stockinet Properties:

Stretching in Length Direction

A sample of stockinet, (either MS02 or MS04 (3M Company, St. Paul, Minn.), nominally 2 or 4 inches in stockinet width) was measured and marked at 5 inches while relaxed without stretching and was used for testing. The sample was weighed and the weight recorded.

The sample was then clamped ½ inch in from each edge in the length direction, leaving an unclamped length of 4 inches. For basis weight determination the sample weight in length stretched samples was adjusted to 80% of the weight of the test sample since 80% of the total clamped sample (which has ½ inch outside the tested area on each end) was free to stretch. A 1 lb. weight was added to the bottom clamp and very slowly and gently released so as not to jerk the sample. The sample was allowed to hang suspended from the top clamp.

The stretched length was recorded after it had reached a constant length (usually waiting for 10 seconds). The average width of the stretched stockinet was measured at least 4 points along the length of the sample to give an average stretched width. This was necessary to accurately determine the basis weight under load.

The stretched area was double the product of the average width recorded times the stretch length recorded. Note that the area was doubled to account for the two sides of the stretched tube.

The percent stretch was calculated by the following formula:

(Stretched length−relaxed length)/relaxed length* 100

Stretching in Width Direction

A sample of stockinet, (either 3M MS02 or MS04, nominally 2 or 4 inches in stockinet width) measured and marked at 2.0 inches long while relaxed without stretching was used for this testing. The sample was weighed and weight recorded.

A ½" (1.27 cm) diameter rod was placed through the 2" sleeve to suspend it from the top and a ½" (1.27 cm) diameter×4" long rod was placed through the 2" sleeve resting at the bottom of the sleeve. A wire was connected to both ends of the lower rod without touching the sample and a 1 lb. weight was suspended from the wire. The weight of the rod and wire was 55.40 g.

The 1 lb weight was gently and slowly released to extend the fabric without jerking the sample. After 10 seconds or sufficient time for the stretched fabric to stabilize and reach a constant stretched length, the length was measured and recorded as the stockinet "width stretch". The "width stretch" was taken as the length of stockinet measured from the outside edges of the two bars supporting the fabric.

The average width of the stretched stockinet was determined by measuring the width at no less than 4 points along the length to arrive at an average stretched width. The stretched area was double the product of the average width recorded times the "width stretch" recorded. Note that the area was doubled to account for the two sides of the stretched tube.

The percent width stretch was calculated by the following formula:

(Stretched width−relaxed width)/relaxed width*100

Porosity

The porosity of the hydrophobic layer of cast padding was tested using a W & L. E. Gurley Densometer Model 4110 (Troy, N.Y.). The "Gurley" densometer or flow through time was measured on a densometer of the type sold under the trade designation "Model 4110" densometer by W. & L. E. Gurley of Troy, N.Y., which was calibrated and operated with a Gurley-Teledyne sensitivity meter (Cat. No. 4134/4135). The "Gurley" densometer time was determined in a manner similar to that specified in ASTM D726-58. "Gurley value" was the time it takes for 100 cc of air at 124 mm (4.88 in.) water pressure to pass through a sample of the web having a circular cross-sectional area of approximately 645 mm$^2$ (1 square inch). The test was run by measuring the time it takes 300 cc to pass through and dividing by 3 to give the time for 100 cc to pass through the sample. The testing was conducted at a temperature of approximately 23° C. and 50 percent relative humidity.

Thickness of Nonwoven Padding

Nonwoven padding was measured for thickness using an Ames Bench Comparator Model #2 (Melrose, Mass.) using the following procedure. The dial micrometer has a thickness range of 0.250 inches calibrated in 0.001 inch increments. The support anvil of the micrometer has a working surface with a minimum of 2 inches in diameter and the pressure contact was a 1.596 inch (4.05 cm) diameter aluminum part (Ames Part No. P-500-1.596). A roll of padding was used as a sample for testing. The dial indicator was adjusted to read zero when the pressure contact was flush with the anvil. The sample roll was unrolled being careful to avoid altering the natural state of the nonwoven. The pressure contact was lowered onto the face of the sample at least ¼ inch away from its edge. The thickness reading was then read off the micrometer. An additional 4 readings were taken of thickness at spots separated by at least 6 inches from the other readings. The five readings were averaged and the result recorded as the thickness measurement for the padding.

Apparent Surface Energy Test

The method for measuring the surface energy is AATCC Test Method 118-1983, with the modifications described below. Surface energies measured according to this modified test method are hereinafter referred to as "apparent" surface energies.

AATCC test method 118-1983 determines the surface energy of a fabric by evaluating the fabric's resistance to wetting by a series of selected hydrocarbon compositions. The hydrocarbons set forth in AATCC 118-1983, however, only provide for measurements of surface tension from about 19.8 to 27.3 dynes per centimeter at 25° C. This range is extended by employing various mixtures of methanol and water in the fabric resistance test. The compositions and their representative surface tensions are as follows. Surface tensions are taken directly or interpolated from Handbook of Chemistry and Physics, 56th Edition, CRC Press, pp. F-42 and F-43. The surface tensions are shown in Tables 1 and 2.

TABLE 1

| Liquid No. | Composition | Surface Tension (dynes/cm at 25° C.) |
| --- | --- | --- |
| 1 | n-heptane | 19.8 |
| 2 | n-octane | 21.4 |
| 3 | n-decane | 23.5 |
| 4 | n-dodecane | 24.7 |
| 5 | n-tetradecane | 26.4 |
| 6 | n-hexadecane | 27.3 |

TABLE 2

| Liquid No. | Volume % Methanol/Water | Surface Tension (dynes/cm at 20° C.) |
| --- | --- | --- |
| 7 | 65/35 | 30 |
| 8 | 53/47 | 35 |
| 9 | 40/60 | 40 |
| 10 | 25/75 | 45 |
| 11 | 21/79 | 50 |
| 12 | 15/85 | 55 |
| 13 | 8.5/91.5 | 60 |
| 14 | 5/95 | 65 |
| 15 | 0/100 | 73 |

The test procedure is as follows. A specimen of the padding is placed flat on a smooth, horizontal surface at 23° C. and 50 percent relative humidity. The method of AATC 118-1983 is used except that beginning with the lowest number test liquid, 5 drops of the liquid are placed on the surface of the fabric in various locations. If three of the five drops wick into the fabric within 60 seconds, the test is reported using the fluid of the next higher surface tension. When at least 3 drops remain on the surface after 60 seconds, the apparent surface energy is the range between the last two liquids used.

Example 1

The cast padding system was a two component system, comprising: a hidrophilic (water absorbing) stockinet, and a hydrophobic (water repellent) nonwoven padding. The stockinet and nonwoven padding are characterized below.

The Stockinet:

The hydrophilic stockinet was prepared from a 18/1 cotton count spun polyester yarn supplied by Carolina Mills Inc., Maiden N.C. made from DAK type 40H polyester. This yarn was knit on a tubular knitter. The knit had 20 courses/inch and 17 wales per inch measured in a relaxed (unstretched) state. The stockinet was knit in nominal relaxed widths from 2 to 5 inches wide. The 2 inch(MS02) and 4 inch(MS04) width properties were measured as described herein. The MS02 and MS04 stockinet samples are available from 3M Co, St. Paul, Minn. as Cat # MS02 and MS04, 3M SCOTCHCAST polyester stockinet material.

The following values were the results of testing 5 samples in the length direction for each stockinet tested and 4 samples in width direction for each stockinet tested. The values are the average of those tests.

TABLE 2

STOCKINET PROPERTIES

| | Test direction | | | |
|---|---|---|---|---|
| | LENGTH | | WIDTH | |
| | Sample | | | |
| | MS04 | MS02 | MS04 | MS02 |
| Weight (g) | 5.40 | 2.46 | 2.26 | 1.02 |
| Stretch length in cm(in) | 11.3(4.45) | 11.5(4.52) | 38.9(15.3) | 22.8(8.97) |
| % Stretch | 11.2 | 13.1 | 283 | 348 |
| Area, relaxed (cm²) | 250 | 129 | 103 | 52 |
| Area, stretched (cm²) | 206 | 95 | 124 | 55 |
| Basis weight, relaxed, (g/m²) | 216 | 191 | 218 | 198 |
| Basis weight, stretched(g/m²) | 209 | 208 | 183 | 184 |
| Width, perpendicular to test direction, relaxed, cm(in) | 9.86(3.88) | 5.08(2.0) | 5.08(2.0) | 5.08(2.0) |
| Width, perpendicular to test direction, stretched cm(in) | 9.12(3.59) | 4.11(1.62) | 1.59(0.62) | 1.22(0.48) |

Apparent Surface Energy of stockinet: 5 drops of deionized water were placed on the surface of the stockinet in the relaxed (not stretched) condition according to the method described herein. All 5 drops soaked into the fabric for both the MS02 and MS04 fabrics.

Nonwoven Padding:

Staple Fiber was purchased from FiberVisions Inc, Covington, Ga. as T190 1.5 inch polypropylene staple fiber. This fiber had a water repellent silicone finish and the following properties:

| | | |
|---|---|---|
| % Elongation | 323-397 | ASTM D-76 & D-2101 |
| Crimp per inch | 13.2-19.8 | ASTM 3937-94 |
| Denier | 2.09-2.41 | ASTM D-1577 |
| % Finish | 0.17-0.39 | ASTM D-2257 |
| Color | white | |

The yarn was free of binders, fillers, and optical brighteners. This fiber was carded into a nonwoven padding which was slit to rolls that were nominally 2, 3, 4, and 6" wide. The padding had the following properties:

| | |
|---|---|
| Basis weight | 8.30 grams/sq ft |
| Tensile strength | 0.3-1 lbs/lineal inch width (target 0.5 lb/lineal inch width) |
| Thickness | 0.030-0.050" measured using the procedure described in the Test Procedure section |
| Rolls | 144" long rolls have diameters of 2.3-3.0" (target 2.6") |
| Repellency Test | Surface tension of less than 30 dyne/cm as measured by the apparent surface energy method described in Test Procedure section (repelled 65/35 methanol/water solution by volume). |
| Porosity | Gurley value of 0.2-0.3 seconds to pass 300 cc, measured as described in Test Procedure. |

Example 2

Wet or Dry Study with or without Stockinet

A study was undertaken using 16 healthy volunteers. The purpose of the study was to assess skin condition under the cast as well as the cast durability over a period of 4 days and 4 nights.

Two combinations of undercast materials were evaluated in the study: the first was a combination of hydrophobic padding (silicone treated polypropylene cast padding 6" described in Example 1 as "nonwoven padding") with polyester stockinet 3" material (available from 3M Co, St. Paul, Minn. as Cat # MS03, 3M SCOTCHCAST polyester stockinet material 3") and the second was the same padding without the stockinet. These materials are characterized in Example 1.

The materials were constructed into short-leg walking casts using 3M SCOTCHCAST PLUS EP casting tape (available from 3M Co. St. Paul, Minn. as 3M SCOTCHCAST Synthetic casting tape, 4") over both undercast combinations.

The 16 subjects were divided into 2 groups of 8 by random selection and all were inspected to confirm good skin health where the cast was to be applied. The casts were lower leg, weight-bearing casts applied to the left leg of each subject. One of the undercast material combinations was applied followed by SCOTCHCAST PLUS casting tape to complete the cast application which took about 30 minutes. The subjects were kept at the clinical site for 20 minutes after the cast application and asked to limit activity level for two additional hours. The cast covered the circumference of the leg from just above mid-calf down over the heel and foot area and ended just proximal to the toes. Cast application and removal was done by an experienced clinician. Cast shoes were provide for each subject to wear over the cast. The subjects were encouraged to bath and/or swim with the casts during the 4 days and 4 nights that the casts were in place. On study day 5 the casts were removed and skin condition assessed by an experienced clinician.

Maceration Assessments Were Defined as Follows:
None=none=0
Mild=pale and slightly puckered=1
Moderate=skin is white and noticeably puckered=2
Severe=skin is cracked and very white=3

There were 2 subjects with a moderate maceration score as opposed to mild or none with the other 14 subjects.

Both subjects were interviewed later in the day regarding the maceration. Both subjects felt that their skin condition had returned to its pre-cast state. None of the subjects showed a severe rating. The results are presented in Table 3 below.

TABLE 3

| | Maceration Rating after 96 Hours | | | | | | | |
|---|---|---|---|---|---|---|---|---|
| | Frequency of Maceration at Rating | | | | | | | |
| Undercast | 0 | | 1 | | 2 | | 3 | |
| treatment | N | % | N | % | N | % | N | % |
| Stockinet & Padding | 3 | 37.5 | 5 | 62.5 | 0 | 0.0 | 0 | 0.0 |
| Padding only | 3 | 37.5 | 3 | 37.5 | 2 | 25.0 | 0 | 0.0 |

N - number of subjects at rating level;
% - percentage of subjects with treatment that had this rating.

The addition of the hydrophilic stockinet added for patient comfort did not result in any additional skin maceration.

Example 3

Comparison to Current Use Product

Casts were constructed using the silicone treated hydrophobic cast padding of Example 1 and the hydrophilic polyester knitted stockinet of Example 1. This evaluation was done by nine evaluation sites of which 8 are were using or had used the commercially available wetable padding (GORE Cast Liner, available from W. L. Gore & Associates, Newark, Del.). Each site applied at least 10 short leg casts and at least 10 short arm casts using the hydrophilic stockinet in combination with the silicone treated polypropylene nonwoven cast padding material made according to Example 1. The sites were supplied with a questionnaire rating the performance of the Wet or Dry relative their current system.

The rating scale for the comparison portion of the questionnaire was as follows:

1=Cast padding system performs much worse than my current wetable padding system 2=Cast padding system performs worse than my current wetable padding system 3=Cast padding system performs the same as than my current wetable padding system 4=Cast padding system performs better than my current wetable padding system 5=Cast padding system performs much better than my current wetable padding system The casts were numbered in order of entry into the evaluation. Upon removal of the cast an acceptance rating was given to each patient. At the conclusion of the evaluation the questionnaire was completed.

There were a total of 248 casts removed and scored. Of the 248 casts scored there were 5 ratings of "3" (same as current wetable material) and the rest were scored "4" or higher. There was no score lower than "3" of the 248 casts removed.

Example 4

A sample of GORE Cast Liner and the cast padding described in Example 1 as the nonwoven padding were tested for porosity as described herein. The Gore Cast Liner product is a composite structure of a middle foam padding layer sandwiched between two microporous films. The hydrophobic microporous expanded polytetrafluoroethylene membrane films are water impermeable but are said to be water vapor permeable. When multiple samples of the GORE cast liner were tested for the porosity value, the porosity value for all samples was measured at greater than 1500 seconds for 300 cc of air to pass (<500 seconds for 100 cc of air to pass). The porosity of the hydrophobic non-woven polypropylene padding (Example 1) was found to be between 0.2-0.3 seconds to pass 300 cc (0.07-0.1 sec/100 cc) of air at 23 C and 50% relative humidity for a minimum of 4 test samples.

What is claimed is:

1. An orthopedic cast system, comprising:
a hydrophilic inner layer having an apparent surface energy greater than 60 dynes per centimeter;
a hydrophobic outer layer having opposing surfaces, wherein the hydrophobic outer layer is located adjacent to said hydrophilic inner layer, and wherein the hydrophobic layer has an apparent surface energy less than about 60 dynes per centimeter; and
a curable casting material disposed on one of the opposing surfaces.

2. The orthopedic casting system of claim 1, wherein the hydrophilic layer has an apparent surface energy greater than about 70 dynes per centimeter.

3. The orthopedic cast system of claim 1, wherein the hydrophilic layer is selected from the group comprising a woven fabric, non-woven fabric, knit fabric or open cell foam.

4. The orthopedic cast system of claim 1, wherein the hydrophilic layer is free of a film.

5. The orthopedic cast system of claim 1, wherein the hydrophilic layer is a composite structure.

6. The orthopedic cast system of claim 1, wherein the hydrophilic layer has a porosity of less than about 60 seconds.

7. The orthopedic casting system of claim 1, wherein the hydrophilic layer has a porosity of less than about 15 seconds.

8. The orthopedic cast system of claim 1, wherein the hydrophilic layer has a basis weight of less than 400 grams per square meter.

9. The orthopedic cast system of claim 1, wherein the hydrophilic layer has a basis weight of at least 100 grams per square meter.

10. The orthopedic cast system of claim 1, wherein the hydrophilic layer has a discontinuous coating of an elastomer.

11. The orthopedic cast system of claim 10, wherein the coating has a static coefficient of friction greater than 1.0.

12. The orthopedic cast system of claim 1, wherein the hydrophobic layer comprises water repellent padding.

13. The orthopedic cast system of claim 12, wherein the hydrophilic layer is a material comprising a cotton, polyester, nylon, acrylic, or rayon fibers or a open cell foam.

14. The orthopedic cast system of claim 1, wherein the hydrophobic outer layer material is treated to render it hydrophobic.

15. The orthopedic cast system of claim 1, wherein the hydrophobic outer layer material is inherently hydrophobic.

16. The orthopedic cast system of claim 1, wherein the hydrophobic layer has a basis weight of at least 40 grams per square meter.

17. The orthopedic cast system of claim 1, wherein the hydrophobic layer has an apparent surface energy less than about 50 dynes per centimeter.

18. The orthopedic casting system of claim 1, wherein the hydrophobic layer has an apparent surface energy less than about 40 dynes per centimeter.

19. The orthopedic cast system of claim 1, wherein the hydrophobic layer has been treated with a substantive compound.

20. The orthopedic cast system of claim 19, wherein the substantive compound is selected from the group consisting of a fluorochemical, silicone, or hydrocarbon.

21. The orthopedic cast system of claim 1, wherein the hydrophobic layer has been fabricated from an inherently hydrophobic fiber.

22. The orthopedic cast system of claim 19, wherein the substantive compound is present in the amounts of between 0.25 to 2.5% by weight of the hydrophobic layer.

23. The orthopedic cast system of claim 19, wherein the substantive compound is non-irritating to the skin.

24. The orthopedic cast system of claim 1, wherein the hydrophobic layer has a porosity of less than about 15 seconds.

25. The orthopedic cast system of claim 1, wherein the hydrophobic layer has a porosity of less than about 10 seconds.

26. The orthopedic cast system of claim 1, wherein the curable casting material comprises a web that is impregnated with a compound that has been cured.

27. The orthopedic cast system of claim 26, wherein the cured compound is cured polyurethane.

28. The orthopedic casting system of claim 26, wherein the cured compound is cured plaster of Paris.

29. A method of immobilizing a body part, the method comprising:
   applying a cast padding system, the cast padding system comprising;
      a hydrophilic inner layer having an apparent surface energy greater than 60 dynes per centimeter;
      a hydrophobic outer layer having opposing surfaces wherein the hydrophobic outer layer is located adjacent to said hydrophilic layer, and wherein the hydrophobic layer has with an apparent surface energy less than about 60 dynes per centimeter; and
      applying a curable casting material to one of the opposing surfaces ; and
      allowing the curable casting material to cure.

30. The method of immobilizing a body part according to claim 29, wherein the hydrophilic layer has an apparent surface energy greater than about 70 dynes per centimeter.

31. The method of immobilizing a body part according to claim 29, wherein the hydrophilic layer is selected from the group comprising a woven fabric, non-woven fabric, knit fabric or open cell foam.

32. The method of immobilizing a body part according to claim 29, wherein the hydrophilic layer is free of a film.

33. The method of immobilizing a body part according to claim 29, wherein the hydrophilic layer is a composite structure.

34. The method of immobilizing a body part according to claim 29, wherein the hydrophilic layer has a porosity of less than about 60 seconds.

35. The method of immobilizing a body part according to claim 29, wherein the hydrophilic layer has a porosity of less than about 15 seconds.

36. The method of immobilizing a body part according to claim 29, wherein the hydrophilic layer has a basis weight of less than 400 grams per square meter.

37. The method of immobilizing a body part according to claim 29, wherein the hydrophilic layer has a basis weight of at least 100 grams per square meter.

38. The method of immobilizing a body part according to claim 29, wherein the hydrophilic layer has a discontinuous coating of an elastomer.

39. The method of immobilizing a body part according to claim 38, wherein the coating has a static coefficient of friction greater than 1.0.

40. The method of immobilizing a body part according to claim 29, wherein the hydrophobic layer comprises water repellent padding.

41. The method of immobilizing a body part according to claim 29, wherein the hydrophilic layer is selected from the group comprising a cotton, polyester, nylon, acrylic, or rayon fibers or a open cell foam.

42. The method of immobilizing a body part according to claim 29, wherein the hydrophobic outer layer material is treated to render it hydrophobic.

43. The method of immobilizing a body part according to claim 29, wherein the hydrophobic outer layer material is inherently hydrophobic.

44. The method of immobilizing a body part according to claim 29, wherein the hydrophobic layer has a basis weight of at least 40 grams per square meter.

45. The method of immobilizing a body part according to claim 29, wherein the hydrophobic layer has an apparent surface energy less than about 50 dynes per centimeter.

46. The method of immobilizing a body part according to claim 29, wherein the hydrophobic layer has an apparent surface energy less than about 40 dynes per centimeter.

47. The method of immobilizing a body part according to claim 29, wherein the hydrophobic layer has been treated with a substantive compound.

48. The method of immobilizing a body part according to claim 47, wherein the substantive compound is selected from the group consisting of a fluorochemical, silicone, or hydrocarbon.

49. The method of immobilizing a body part according to claim 29, wherein the hydrophobic layer has been fabricated from an inherently hydrophobic fiber.

50. The method of immobilizing a body part according to claim 47, wherein the substantive compound is present in the amounts of between 0.25 to 2.5% by weight of the hydrophobic layer.

51. The method of immobilizing a body part according to claim 47, wherein the substantive compound is non-irritating to the skin.

52. The method of immobilizing a body part according to claim 29, wherein the hydrophobic layer has a porosity of less than about 15 seconds.

53. The method of immobilizing a body part according to claim 29, wherein the hydrophobic layer has a porosity of less than about 10 seconds.

54. The method of immobilizing a body part according to claim 29, wherein the curable casting material comprises a web that is impregnated with a compound that has been cured.

55. The method of immobilizing a body part according to claim 54, wherein the compound is polyurethane

56. The method of immobilizing a body part according to claim 54, wherein the cured compound is cured plaster of Paris.

57. An orthopedic cast kit comprising:
a hydrophilic inner layer having an apparent surface energy greater than 60 dynes per centimeter; and
a hydrophobic outer layer having opposing surfaces, wherein the a hydrophobic outer layer is located adjacent to said hydrophilic inner layer, and wherein the hydrophobic layer has an apparent surface energy less than about 60 dynes per centimeter.

58. The orthopedic cast kit of claim 57, further comprising a curable casting material.

59. An orthopedic cast system, comprising:
a hydrophilic inner layer having a discontinuous coating of an elastomer;
a hydrophobic outer layer having opposing surfaces, wherein the a hydrophobic outer layer is located adjacent to said hydrophilic inner layer, wherein the hydrophobic layer has an apparent surface energy less than about 60 dynes per centimeter; and a curable casting material disposed on one of the opposing surfaces.

60. The orthopedic cast system of claim 59, wherein the hydrophilic layer has an apparent surface energy greater than 60 dynes per centimeter.

61. The orthopedic cast system of claim 59, wherein the hydrophilic layer is free of a film.

62. The orthopedic cast system of claim 59, wherein the hydrophilic layer has a porosity of less than about 60 seconds.

63. The orthopedic cast system of claim 59, wherein the hydrophilic layer has a basis weight of less than 400 grams per square meter.

64. The orthopedic cast system of claim 59, wherein the coating has a static coefficient of friction greater than 1.0.

65. The orthopedic cast system of claim 59, wherein the hydrophilic layer is a material comprising a cotton, polyester, nylon, acrylic, or rayon fibers or a open cell foam.

66. The orthopedic cast system of claim 59, wherein the hydrophobic outer layer is treated to render it hydrophobic.

67. The orthopedic cast system of claim 59, wherein the hydrophobic outer layer is inherently hydrophobic.

68. The orthopedic cast system of claim 59, wherein the hydrophobic layer has a basis weight of at least 40 grams per square meter.

69. The orthopedic cast system of claim 59, wherein the hydrophobic layer has been treated with a substantive compound.

70. The orthopedic cast system of claim 69, wherein the substantive compound is selected from the group consisting of a fluorochemical, silicone, or hydrocarbon.

71. The orthopedic cast system of claim 59, wherein the hydrophobic layer has been fabricated from an inherently hydrophobic fiber.

72. The orthopedic cast system of claim 59, wherein the hydrophobic layer has a porosity of less than about 15 seconds.

73. An orthopedic cast system, comprising:
a hydrophilic inner layer;
a hydrophobic outer layer having opposing surfaces, wherein the hydrophobic layer is located adjacent to said hydrophilic inner layer, wherein the hydrophobic layer is inherently hydrophobic and has an apparent surface energy less than about 60 dynes per centimeter; and
a curable casting material disposed on one of the opposing surfaces.

74. The orthopedic cast system of claim 73, wherein the hydrophilic layer has an apparent surface energy greater than 60 dynes per centimeter.

75. The orthopedic cast system of claim 73, wherein the hydrophilic layer is free of a film.

76. The orthopedic cast system of claim 73, wherein the hydrophilic layer has a porosity of less than about 60 seconds.

77. The orthopedic cast system of claim 73, wherein the hydrophilic layer has a basis weight of less than 400 grams per square meter.

78. The orthopedic cast system of claim 73, wherein the hydrophilic layer has a discontinuous coating of an elastomer.

79. The orthopedic cast system of claim 78, wherein the coating has a static coefficient of friction greater than 1.0.

80. The orthopedic cast system of claim 73, wherein the hydrophilic layer is a material comprising a cotton, polyester, nylon, acrylic, or rayon fibers or a open cell foam.

81. The orthopedic cast system of claim 73, wherein the hydrophobic layer has a basis weight of at least 40 grams per square meter.

82. The orthopedic cast system of claim 73, wherein the hydrophobic layer has been fabricated from an inherently hydrophobic fiber.

83. The orthopedic cast system of claim 73, wherein the hydrophilic layer has a porosity of less than about 15 seconds.

84. An orthopedic cast system, comprising:
a hydrophilic inner layer;
a hydrophobic outer layer having opposing surfaces adjacent to said hydrophilic inner layer, wherein the hydrophobic layer has an apparent surface energy less than about 60 dynes per centimeter and wherein the hydrophobic layer has been fabricated from an inherently hydrophobic fiber; and
a curable casting material disposed on one of the opposing surfaces.

85. The orthopedic cast system of claim 84, wherein the hydrophilic layer has an apparent surface energy greater than 60 dynes per centimeter.

86. The orthopedic cast system of claim 84, wherein the hydrophilic layer is free of a film.

87. The orthopedic cast system of claim 84, wherein the hydrophilic layer has a porosity of less than about 60 seconds.

88. The orthopedic cast system of claim 84, wherein the hydrophilic layer has a basis weight of less than 400 grams per square meter.

89. The orthopedic cast system of claim 84, wherein the hydrophilic layer has a discontinuous coating of an elastomer.

90. The orthopedic cast system of claim 89, wherein the coating has a static coefficient of friction greater than 1.0.

91. The orthopedic cast system of claim 84, wherein the hydrophilic layer is a material comprising a cotton, polyester, nylon, acrylic, or rayon fibers or a open cell foam.

92. The orthopedic cast system of claim 84, wherein the hydrophobic outer layer is treated to render it hydrophobic.

93. The orthopedic cast system of claim 84, wherein the hydrophobic outer layer is inherently hydrophobic.

94. The orthopedic cast system of claim 84, wherein the hydrophobic layer has a basis weight of at least 40 grams per square meter.

95. The orthopedic cast system of claim 84, wherein the hydrophobic layer has been treated with a substantive compound.

96. The orthopedic cast system of claim 95, wherein the substantive compound is selected from the group consisting of a fluorochemical, silicone, or hydrocarbon.

97. The orthopedic cast system of claim 84, wherein the hydrophobic layer has a porosity of less than about 15 seconds.

* * * * *

UNITED STATES PATENT AND TRADEMARK OFFICE
CERTIFICATE OF CORRECTION

PATENT NO.       : 7,438,697 B2
APPLICATION NO.  : 11/235382
DATED            : October 21, 2008
INVENTOR(S)      : Anthony J. Campagna It is certified that error appears in the above-identified patent and that said Letters Patent is hereby corrected as shown below:

Column 2:
　　　Line 50, After "layer" insert -- . --.

Column 6:
　　　Line 25, Delete "yams," and insert -- yarns, --, therefor.

Column 8:
　　　Line 10, Delete "Rf" and insert -- $R_f$ --, therefor.

Column 11:
　　　Line 9, Delete "least" and insert -- at least --, therefor.

Column 13:
　　　Line 15, Delete "hidrophilic" and insert -- hydrophilic --, therefor.

Column 15:
　　　Line 46, Delete "are were" and insert -- were --, therefor.

Column 17:
　　　Line 2, In Claim 14, after "layer" delete "material".

Column 17:
　　　Line 5, In Claim 15, after "layer" delete "material".

Column 17:
　　　Line 51, In Claim 29, after "has" delete "with".

Column 18:
　　　Line 27, In Claim 42, after "layer" delete "material".

Column 18:
　　　Line 30, In Claim 43, after "layer" delete "material".

Column 19:
　　　Line 2, In Claim 55, after "polyurethane" insert -- . --.

UNITED STATES PATENT AND TRADEMARK OFFICE
CERTIFICATE OF CORRECTION

PATENT NO. : 7,438,697 B2
APPLICATION NO. : 11/235382
DATED : October 21, 2008
INVENTOR(S) : Anthony J. Campagna It is certified that error appears in the above-identified patent and that said Letters Patent is hereby corrected as shown below:

<u>Column 19:</u>
    Line 10, In Claim 57, delete "the a" and insert -- the --, therefor.

<u>Column 19:</u>
    Line 20, In Claim 59, delete "the a" and insert -- the --, therefor.

Signed and Sealed this

Thirtieth Day of December, 2008

JON W. DUDAS
*Director of the United States Patent and Trademark Office*